(12) United States Patent
Riesinger

(10) Patent No.: US 8,846,109 B2
(45) Date of Patent: Sep. 30, 2014

(54) TREATMENT SOLUTION FOR TREATING WOUNDS, IN PARTICULAR FOR LIQUID WOUND TREATMENT

(75) Inventor: Thomas Riesinger, Nuremberg (DE)

(73) Assignee: Nawa Heilmittel GmbH, Nürnberg (DE)

( * ) Notice: Subject to any disclaimer, the term of this patent is extended or adjusted under 35 U.S.C. 154(b) by 160 days.

(21) Appl. No.: 13/148,406

(22) PCT Filed: Feb. 5, 2010

(86) PCT No.: PCT/DE2010/000129
§ 371 (c)(1),
(2), (4) Date: Aug. 8, 2011

(87) PCT Pub. No.: WO2010/091661
PCT Pub. Date: Aug. 19, 2010

(65) Prior Publication Data
US 2011/0318428 A1    Dec. 29, 2011

(30) Foreign Application Priority Data
Feb. 13, 2009 (DE) .......................... 10 2009 008 919

(51) Int. Cl.
| | | |
|---|---|---|
| A01N 59/16 | (2006.01) | |
| A61K 33/26 | (2006.01) | |
| A61K 33/32 | (2006.01) | |
| A01N 37/52 | (2006.01) | |
| A61K 31/155 | (2006.01) | |
| A61K 31/295 | (2006.01) | |
| A61K 45/06 | (2006.01) | |
| A61K 31/315 | (2006.01) | |
| A61K 31/205 | (2006.01) | |
| A61K 33/30 | (2006.01) | |

(52) U.S. Cl.
CPC .............. *A61K 45/06* (2013.01); *A61K 31/155* (2013.01); *A61K 31/295* (2013.01); *A61K 31/315* (2013.01); *A61K 31/205* (2013.01); *A61K 33/30* (2013.01); *A61K 33/26* (2013.01)
USPC .......................... 424/646; 424/641; 514/635

(58) Field of Classification Search
CPC ............ A61K 2300/00; A61K 31/205; A61K 31/295; A61K 31/315; A61K 33/26; A61K 33/30; A61K 8/19; C07D 213/81; A61Q 19/00; A61Q 17/005; A61L 2300/404; A61N 5/0616
See application file for complete search history.

(56) References Cited

U.S. PATENT DOCUMENTS

| | | | | |
|---|---|---|---|---|
| 3,150,081 | A * | 9/1964 | Harris ........................... | 210/698 |
| 5,244,666 | A * | 9/1993 | Murley ......................... | 424/405 |
| 2004/0076686 | A1* | 4/2004 | Riesinger ...................... | 424/642 |
| 2010/0233289 | A1* | 9/2010 | Smithyman et al. .......... | 424/637 |
| 2011/0171283 | A1 | 7/2011 | Riesinger | |

FOREIGN PATENT DOCUMENTS

| | | |
|---|---|---|
| DE | 3537627 | 5/1986 |
| DE | 10139398 | 7/2002 |
| DE | 102007030931 | 1/2009 |
| EP | 0 363 696 A1 | 4/1990 |
| WO | WO 00/33829 A1 | 6/2000 |
| WO | WO 0141727 A1 * | 6/2001 |
| WO | WO 03/004013 A1 | 1/2003 |

OTHER PUBLICATIONS

Fabry et al (Bacterial decontamination of surgical wounds treated with Lavasept, Mar. 2006, International Journal of Hygiene and Environmental Health, vol. 209, pp. 567-573).*
Kaehn et al (Polyhexanide (PHMB) and Betaine in Wound Care Management, May 2008, EWMA Journal, vol. 8, p. 13).*
EPA, (Iron Mountain Mine Superfund Site, website http://yosemite.epa.gov/r9/sfund/r9sfdocw.nsf/ViewByEPAID/CAD980498612, 2013).*
Noguchi et al (pH-value, and Iron, Copper, and Zinc content of the soils at Yumoto Area of Narugo Hot Springs, Miyagi Prefecture, j-hss.org, vol. 23, 2014).*
ARRI, (What Causes Foam in Streams and Lakes?, website http://www.arrialaska.org/foam-in-streams.html, 2014).*
Wehr et al (Hydrobiologia, vol. 98, pp. 97-105, 1983).*
Fabry W. et al. "Bacterial decontamination of surgical wounds treated with Lavasept", Int. J. Hyg. Environ.-Health 209 (2006) 567-573.

* cited by examiner

*Primary Examiner* — Brian-Yong Kwon
*Assistant Examiner* — Mark V Stevens
(74) *Attorney, Agent, or Firm* — Welsh Flaxman & Gitler LLC

(57) ABSTRACT

The invention relates to a treatment solution for treating wounds, preferably for liquid wound treatment of acute and chronic wounds, made of an aqueous solution including zinc, iron, and acid, wherein the per liter proportion of zinc is 10 to 100 mg, the proportion of iron is 6.5 to 60 mg, and the proportion of acid is selected such that the pH value of the treatment solution is 2.5 to 3.5.

3 Claims, No Drawings

TREATMENT SOLUTION FOR TREATING WOUNDS, IN PARTICULAR FOR LIQUID WOUND TREATMENT

BACKGROUND OF THE INVENTION

The invention relates to a treatment solution and in particular to a treatment solution for liquid wound treatment, in which the wound to be treated is maintained in a liquid state with a sufficiently large volume of treatment liquid. This treatment results in accelerated wound healing with optimized scar formation.

A treatment solution for liquid wound treatment is known in the art (DE 101 39 398 A1). The known treatment solution consists of an aqueous solution comprising zinc in the form of $ZnCl_2$, iron in the form of $FeSO_4$ and an inorganic acid in such proportions that the solution contains 10-100 mg of zinc and 6.5-65 mg of iron per liter of liquid and the pH value of the solution is regulated to a value between 2.5 and 3.5.

It has been shown that the prior treatment solution achieves very good results in the treatment of postoperative wounds, such results cannot be determined for wound treatment in general, especially not for the treatment of acute and chronic wounds.

It is an object of the invention is to present a treatment solution which achieves optimal treatment results in general for the treatment of acute and chronic wounds, i.e. fast wound healing with optimal scar formation.

SUMMARY OF THE INVENTION

The treatment solution according to the invention is especially suitable for treating
skin lacerations
cuts and abrasions, as well as lacerated wounds
decubital ulcers
arterio-venous ulcers
diabetic ulcers
1st and 2nd degree burns
for moistening bandages and wound dressings, such as compresses, gauze, sponges, alginates, etc.; when changing bandages, for dissolving encrusted bandages or other encrusted wound dressings.

The treatment solution according to the invention consists of an aqueous solution comprising in addition to zinc and iron, at least one tenside, for example cocamidopropyl betaine, and an antiseptic component in the form of polyhexanide, preferably in the form of PHMB or polyaminopropyl biguanide.

DETAILED DESCRIPTION OF THE INVENTION

The components of the treatment solution, according to the invention, support each other in a synergetic manner, so that the liquid wound treatment solution can be used for acute and chronic wounds and achieves the desired results.

The special composition of the treatment solution, according to the invention, causes a synergetic effect of the components during the treatment of the respective wound in such a manner that first, due to the tenside contained in the solution, protein components, necrotic tissue components, etc. are removed from the wound, so that then in a second stage the antiseptic component can become fully effective for the initial destruction of germs present in the wound, so that then the prerequisites conducive to healing of the wound by the metal ions (iron and zinc) are created and that the respective wound can be kept free of germs by the metal ions during the liquid treatment.

Generally, the treatment solution according to the invention contains the following proportions of the components per liter of solution (especially water):
tenside: 1000-6000 mg
antiseptic component,
in particular polyhexanide: 100-1000 mg
zinc: 10-100 mg
iron: 6.5-60 mg In a preferred embodiment, the treatment solution contains the following proportions of the components per liter of solution (especially water):
tenside: ca. 3000 mg
antiseptic component,
for example polyhexanide: ca. 200 mg
zinc: 15-45 mg
iron: 10-30 mg.

By adding an acid, preferably an inorganic acid, e.g. by adding hydrochloric acid, the pH value of the treatment solution is regulated to a value between 2.5 and 3.5, preferably to a value between 2.75 and 3.5.

The invention claimed is:

1. A treatment solution for liquid wound treatment of acute and chronic wounds, consisting of an aqueous solution of zinc, iron, an inorganic acid, a tenside cocamidopropyl betaine and an antiseptic component of polyhexanide or polyaminopropyl biguanide, wherein a per liter proportion of zinc is from 15-45 mg per liter of solution, a proportion of iron is from 10-30 mg per liter of solution and a proportion of the inorganic acid is selected such that a pH value of the treatment solution is between 2.75 and 3.5, wherein the tenside cocamidopropyl betaine is from 1000-6000 mg per liter of the treatment solution and a proportion of the antiseptic component of polyhexanide or polyaminopropyl biguanide is from 100-1000 mg per liter of the treatment solution.

2. The treatment solution according to claim 1, wherein the proportion of the tenside cocamidopropyl betaine is 3000 mg per liter of solution.

3. The treatment solution according to claim 1, wherein the proportion of the antiseptic component of polyhexanide or polyaminopropyl biguanide is 200 mg per liter of solution.

* * * * *